US007863264B2

(12) United States Patent
Vange et al.

(10) Patent No.: US 7,863,264 B2
(45) Date of Patent: Jan. 4, 2011

(54) STABILISED COMPOSITIONS HAVING ANTIBACTERIAL ACTIVITY

(75) Inventors: Jakob Vange, Helsingoer (DK); Brian Nielsen, Goerloese (DK)

(73) Assignee: Coloplast A/S, Humlebaek (DK)

( * ) Notice: Subject to any disclaimer, the term of this patent is extended or adjusted under 35 U.S.C. 154(b) by 1608 days.

(21) Appl. No.: 10/380,471

(22) PCT Filed: Sep. 26, 2001

(86) PCT No.: PCT/DK01/00616

§ 371 (c)(1), (2), (4) Date: Mar. 20, 2003

(87) PCT Pub. No.: WO02/26039

PCT Pub. Date: Apr. 4, 2002

(65) Prior Publication Data

US 2003/0186955 A1 Oct. 2, 2003

(30) Foreign Application Priority Data

Sep. 29, 2000 (DK) ........................ PA 2000 01451

(51) Int. Cl.
*A01N 55/02* (2006.01)
*A01N 43/54* (2006.01)
*A61K 31/555* (2006.01)
*C07D 239/42* (2006.01)
*C07D 401/04* (2006.01)

(52) U.S. Cl. ...................................... 514/184; 514/256

(58) Field of Classification Search .................. 424/67, 424/405; 514/722, 184, 256
See application file for complete search history.

(56) References Cited

U.S. PATENT DOCUMENTS 2,336,131 A 12/1943 Schaffer ..................... 260/299
3,911,115 A 10/1975 Hadhanyi ................... 424/180
3,930,000 A 12/1975 Margraf ...................... 424/245
4,172,140 A * 10/1979 Shull et al. .................. 514/389
5,298,624 A 3/1994 Lasker ........................ 548/107
5,326,567 A 7/1994 Capelli ....................... 424/405
5,429,819 A 7/1995 Oka et al. .................. 424/400
5,869,494 A * 2/1999 Gulliya ....................... 514/270
6,210,556 B1 4/2001 Toben et al. ................ 205/253
2002/0172709 A1 * 11/2002 Nielsen et al. ............. 424/445

FOREIGN PATENT DOCUMENTS

DE 2012717 10/1970
DK 9800759 12/2000
EP 0 151 942 8/1985
EP 0 272 149 6/1988
EP 0 591 440 1/1996
EP 0 985 390 3/2000
JP 2000-16904 1/2000
WO 93/00056 1/1993
WO 99/41433 8/1999
WO 00/09173 2/2000

OTHER PUBLICATIONS

Aoki et al., "Structure of (1-Methyluracilato) silver (I) ($Ag(C_5H_5N_2O_2)$)]," *Acta Cryst.*, C40: 775-778 (1984).
Guay et al., "Model Compounds for the Interaction of Silver(I) With Polyuridine. Crystal Structure of a 1 : 1 Silver Complex with 1-Methylthymine," *J. Am. Chem. Soc.*, 101(21) : 6260-6263 (1979).
Hopkala, Hanna, "Application of chelate complexes in ion-selective liquid membrane electrodes," *Acta Pol. Pharm.*, 43(3) : 236241 (1986) (Abstract).
Huot et al., "The electrochemical oxidation of silver and tetra-ethylammonium salts of formamides and imides. N,N—Coupling of formanilidyl radicals," *Can. J. Chem.*, 66 : 35-44 (1988).
Menez et al., "Isomères N. et O isopropylès du barbital et du phènobarbital: propriètès physicochimiques et pharmacoloqiques," *Eur. J. Med. Chem.*, 18(6) : 521-529 (1983).
Wysor et al., "Antibacterial Properties of Silver Chelates of Uracil and Uracil Derivatives in vitro," *Chemotherapy*, 17 : 188-199 (1972).

* cited by examiner

*Primary Examiner*—Yong S Chong
(74) *Attorney, Agent, or Firm*—Jacobson Holman PLLC

(57) ABSTRACT

A stabilised composition having antibacterial, antiviral and/or antifungal activity, said composition comprising silver ions and a ligand, characterised in that the composition comprises a complex of silver and a ligand selected from the group consisting of 5,5-disubstituted hydantoins in which the substituents do not comprise conjugated unsaturated bonds and barbituric acid and derivatives thereof stabilising silver ions against reduction to free silver in a hydrophilic environment, and that the composition has a solubility in water higher than 10 mg Ag/l is stable during sterilisation and retains the activity without giving rise to darkening or discoloration of the dressing during storage.

13 Claims, No Drawings

STABILISED COMPOSITIONS HAVING ANTIBACTERIAL ACTIVITY

This is a nationalization of PCT/DK01/00616 filed Sep. 26, 2001 and published in English.

BACKGROUND OF THE INVENTION

1. Field of the Invention

The present invention relates to stabilised compositions having antibacterial, anti-viral and/or antifungal activity, to a method of producing such compositions, medical devices having a coating comprising such compositions, and the use of the stabilised compositions for producing a wound dressing, an ostomy appliance, an incontinence device, other medical devices or hydrophilic coatings.

The antiseptic activity of silver compounds is a well known property which has been utilised for many years. The bacteriostatic and fungistatic effect is caused by the silver ion and a simple compound which has been used clinically is for instance silver nitrate. Silver nitrate in concentrations of 0.5-1% in water shows disinfectant properties and is used for preventing infections in burns or for prophylaxis of neonatal conjunctivitis. For another silver compound, silver sulfadiazine, the antibacterial effect of the sulfadiazine molecule is further enhanced by the complexing with the disinfecting silver ion. In contrast to the silver nitrate, the solubility of the silver sulfadiazine complex is low and hence, both of the two active parts are only present in solution in low concentrations but may be present over a longer period of time before being washed out at site to be treated. The silver sulfadiazine is intensively used in the treatment of wounds, in particular burns, under the trademarks Silvadene® and Flamazine®. Silver-protein-combinations are yet other antiseptic formulations which have been used in low concentrations as eye drops.

2. Description of the Related Art

Bacteriostatics based on the silver ion are further used in various medical devices. One example of such application is the use in the wound dressing sold by Johnson & Johnson under the trademark Actisorb® which is an activated charcoal cloth dressing. Another example is the wound dressing sold under the trademark EZ-Derm by Genetic Laboratories which dressing is a modified pigskin impregnated with a soluble silver compound intended for treatment of burns. A number of patents discloses compositions or devices showing antiseptic properties based on contents of silver compounds. EP 272 149 B1 discloses a medical dressing of the 'hydrocolloid' type containing and releasing active components. Silver chloride is a specific antiseptically acting compound mentioned in this patent.

A specific advantage in using the silver ion as bacteriostatic agent is the general lack of formation of bacterial tolerance to the compound. This is in contrast to many types of antibiotics. However a major drawback when using ionic silver for bacteriostatic purposes is the reduction of the ion to free silver which results in dark staining. Such staining has been reported to give potentially permanent pigmentation of the skin, the so-called argyria. It is commonly recognised that silver containing compounds will discolour by influence of light and or heat, and it will often be found that sterilisation by radiation may lead to a unsatisfactory change of the colour of a composition in which it is comprised, irrespective of the use in a solution, cream or gel or a medical device. Furthermore, such antibacterial compositions are often intended used in connection with medical or cosmetic products under circumstances where a discoloration is very unfortunate and potentially precluding for the use.

Recently, principles of antimicrobial metal-based compositions being photo stable, have been disclosed in U.S. Pat. No. 5,326,567 to Capelli and in U.S. Pat. No. 5,429,819 to Oka. In U.S. Pat. No. 5,326,567 a 'host-guest' relationship between silver ions and acyclic polyethers is accomplished through the use of excess of halide ions. In U.S. Pat. No. 5,429,819 is disclosed a photo-stable composition comprising a complex of the silver ion with a thiosulphate salt carried on a porous particulate carrier. In U.S. Pat. No. 3,911,115 (DE patent No. 22 60 536) a cycloheptaamylose (β-cyclodextrin) alkanol amine compound is claimed to posses stabilising effect on silver. However, in praxis the cycloheptaamylose alkanol amine complex is not effective in preventing discolouring. In U.S. Pat. No. 5,298,624 Lasker claims stable organometallic complexes of 5,5-diphenyl-2,4-imidazolidenedione (diphenylhydantoin) used as biocides. One such material is the silver-diphenyl hydantoin complex, which, however, it is poorly soluble in water. In U.S. Pat. No. 2,336,131 Schaffer disclose the formulation of silver allantoinate for antibacterial use. The compound is intended for medical use. However the compound does not show high stability against light. In U.S. Pat. No. 3,930,000 Margraf discloses silver-zinc allantoinate for topical use for control of bacteria and fungi. These compound, however, show a low solubility. In International Published Patent Application No. WO 00/09173 Pedersen et al teaches the stabilisation of silver by complexing with amines presenting a lone pair of electrons.

It is commonly recognised that compounds containing silver will discolourise in presence of light and/or heat, as well as it often will be found that radiation sterlisation process will lead to a dissatisfactory change of colour of the composition in which it is comprised whether it is in a cream or a gel or a medical device. Moreover, such antibacterial compositions are often intended for use for medical or cosmetic purposes under which circumstances a discoloration is very unfortunate and potentially prevents the use of silver ions for said use.

It is an object of the present invention to provide complex structure rendering silver ions stable against loss of the antiseptic activity and against darkening due to reduction of the silver ions or the formation of darkly stained sparingly or insoluble silver compounds. Furthermore, it is an object to provide a complex structure rendering silver ions available sufficiently quickly and in a sufficiently high and lasting concentration to ensure that an effective antiseptic activity is obtained. Still further it is an object to provide a method for preparing such complexes without losing the antiseptic activity of the silver ions. Further it is the objective to incorporate such into entities in combination with hydrophilic polymers, e.g. in hydrocolloid particles or coatings enabling a sufficient release of silver for the establishment of a bactericidal burst.

Such entities may be medical devices or instruments like catheters, guide-wires, wound dressings or similar.

The use of the silver complex of diphenyl hydantoin as taught by Lasker has the advantage of easy processing and for certain applications slow release. However, it is a major drawback that the compound has low solubility and lacks sufficient stability against irradiation and light. The silver allantionate likewise show low stability against light and has limited solubility. Especially when the compound is used in combination with hydrophilic polymers often used in the context of medical devices it may be impossible to obtain a high release of silver due to low solubility of the compound in biological environments and similarly impossible to incorporate such in the device.

It has surprisingly be found that certain silver complexes comprising silver and a ligand selected from the group consisting of 5,5-disubstituted hydantoins in which the substituents do not comprise conjugated unsaturated bonds and barbituric acid and derivatives thereof possess very good stability.

SUMMARY OF THE INVENTION

The present invention relates to stabilised compositions having antibacterial, antiviral and/or antifungal activity.

Furthermore, the invention relates to a method of producing compositions having antibacterial, antiviral and/or antifungal activity.

Still further, the invention relates to medical devices being coated with, impregnated with or blended during production with stabilised compositions having antibacterial, antiviral and/or antifungal activity.

The invention also relates to a method of treating or preventing infection in a human being by applying a medical device such as a wound dressing or an ostomy appliance, an incontinence device, or other device such as a catheter comprising a hydrophilic coating which medical device comprises a stabilised composition having antibacterial, antiviral and/or antifungal activity.

DETAILED DESCRIPTION OF THE PRESENT INVENTION

The present invention relates in its broadest aspect to a stabilised composition having antibacterial, antiviral and/or antifungal activity which composition is characterised in that it comprises complexes of silver ions and a ligand selected from the group consisting of 5,5-disubstituted hydantoins in which the substituents do not comprise conjugated unsaturated bonds and barbituric acid and derivatives thereof which complexes have a solubility in water higher than 15 mg Ag/l have been found to stabilise the silver ions against darkening by UV light.

Suitable compounds are 5,5-disubstituted hydantoins in which the substituents do not comprise conjugated unsaturated bonds, preferably 5,5-dialkylsubstituted hydantoins and barbituric acid and derivatives thereof, preferably dialkylbarbiturates.

In the present context, "alkyl" is intended to designate straight or branched or cyclic alkyl groups having 1-12 carbon atoms, more preferred 1-6 carbon atoms and most preferred 1-4 carbon atoms such as methyl, ethyl, propyl, isopropyl, n-butyl, isobutyl or tert.butyl. "Cycloalkyl" is intended to designate cyclic alkyl groups comprising 3-15 carbon atoms, preferably 4-10 and most preferred 5-7 carbon atoms. The two moieties may be the same or different.

Hydantoins and barbituric acid derivatives suitable for use in the present invention are also such comprising a further substitution of an alkenyl, alkynyl, acyl moiety.

"Alkenyl" or "alkynyl" are intended to designate straight or branched hydrocarbon groups comprising a carbon-carbon double or triple bond and having 2-12 carbon atoms, preferably 2-6 carbon atoms and most preferred 1-4 carbon atoms. "Acyl" is intended to designate $C_2$-$C_{10}$ alkanoyl, alkenoyl or alkynoyl groups, preferably such groups comprising 2-6 carbon atoms and most preferred 2-4 carbon atoms or aroyl having 1-4 carbon atoms in a side chain. An especially preferred acyl group is the ethanoyl group.

Preferred compositions are such wherein the ligand is an aliphatic or alicyclic substituted hydantoin.

Preferred compounds among the above are 5,5-dimethyl-hydantoin, 5,5-diethyl-hydantoin, 5,5-dipropyl-hydantoin, 1-acetyl-5,5-dimethyl-hydantoin, 5,5-dimethyl-barbituric acid, and 1,5,5-trimethyl-barbituric acid. All these complexes shown a solubility in water above 20 mg Ag/l.

Especially preferred is 5,5-dimethyl hydantoin.

These compositions of the invention have a solubility in water higher than 10 mg Ag/l, preferably more than 15 mg Ag/l and more preferred more than 25 mg Ag/l. The solubility is preferably more than 50 mg Ag/l and most preferred more than 100 mg Ag/l.

In another preferred embodiment of the invention, the composition contains a second silver compound with a solubility less than 10 mg Ag/l. Such compositions provide a graduated release profile both offering high initial release of silver and a prolonged period of silver release at a high level.

The composition of the invention typically comprises complexes of silver and compounds of the formula (I) in the ratio 1:1. In a preferred embodiment, the compound of the formula (I) is present in excess i.e. in ratios of more than 1:1, preferably 1:2. Such complexes show an increased solubility in water.

When providing complexes of the above ligands and silver, a second cation is to be present in order to counterbalance the charge of the ligands. Such counter ions are preferably ions of alkaline metals such as lithium, sodium or potassium, preferably sodium; or ammonium ions.

Furthermore, it has been found that the silver complexes of the invention are stable against reduction by influence from UV light and irradiation in hydrophilic compositions.

It has been found that ligands especially suitable for the purpose of the present invention are 5,5-disubstituted hydantoins and barbiturates in which the substituents do not absorb UV light, i.e. comprising substituents not comprising conjugated unsaturated bonds.

Preferred types of complexes are complexes with hydantoins or barbiturates. In the group of hydantoins the aliphatic or alicyclic substituted hydantoins for instance 5,5-dimethyl hydantoins and 5,5-diethyl hydantoins are preferred due to a very high stability.

In the present context, the term "stable" is intended to cover an improvement of the stability of the silver ion against the influence of UV light which normally leads to formation of dark stained free silver. A preferred stability may be expressed as a distance in CIE-lab Color Space below 25, preferably below 10.

Solid silver or solutions of silver salts may fairly easily be stabilised against heat and UV light when stabilised with dextrins and thiosulfates. These types of complexes has, however, shown not to be stable in presence of hydrophilic polymers especially the strongly polar or ionic polymers. The stabilisation of silver according to the invention also provides stability in the presence of such polymers. As ionic and polar polymers are used increasingly in medical devices and as silver compounds are effective antibacterial agents combinations of these are very desirable. The present invention offers the option of using such combinations without risking discoloration as well as methods of producing such and medical devices comprising the same.

The compositions of the invention may be e.g. used in wound dressings. In particular the material is suitable for incorporation in traditional gauzes and compresses, hydrocolloid dressings or xerogel dressings. In such dressings the silver composition according to the invention may readily be incorporated by dissolution in water and impregnation into dressings like gauze, or they may be introduced as a component of said dressing, e.g. a component of an adhesive composition, by a manner known per se. A method for incorporation in hydrocolloid dressings is disclosed in EP Patent 591,440, Samuelsen et al. A method for incorporation of the composition in alginate fibre dressings or similar dressings is by simply adding the composition to the water based solution comprising the alginate before this is further processed into a fibrous material. Introduction may also take place in the form of a powder which is easily obtained for instance by grinding a lyophilised or spray-dried material. In wound dressings the compound may be introduced into the adhesive for fixing the dressing to the wound site or into another part of the dressing, for instance a foam pad.

The compositions of the invention and formulations thereof may be used for antibacterial, antiviral or antifungal use in the area of human or veterinary medicine. Such formulations may be in the form of a cream or gel intended for dermatological use, in wounds or other body cavities. Formulations may also be in form of powders for similar purposes or for skin folds or athletes foot or the like in the veterinary area.

Not only wound dressings but many other types of products are suitable for incorporation of the silver compositions of the invention for instance foamed products or vaginal inserts for use in the continence care, condoms, male external urine catheters, skin adhesives etc.

Furthermore, the compositions may be used in products not necessarily being in direct contact with the body such as powders for removal of odour in incontinence pads or for incorporation into ostomy pouches.

The silver compositions of the invention may also be used in implants and sutures or materials that are intended to be left for a period in body cavities. This will be advantageous in connection with surgery where the risk of infection is always latent. Systemic prophylactic treatment with antibiotics in combination with a proper antiseptic treatment of the skin are in most cases common practice. Often medical articles that are implanted or for other reasons left in a surgical opening are carrying antiseptics or even antibiotics. The present invention offers an advantageous alternative to known compositions comprising silver as the compositions of the invention have been found to have broad antiseptic properties and to be stable during storing and in use. Moreover, the compositions of the invention are very suitable for controlled release for instance when incorporated in polylactic acid for sutures or implants or when incorporated in implants based on hydroxyl apatite. Furthermore, the silver compositions of the invention are suitable for incorporation into haemostatics based on e.g. alginate fibres or foam dressings as well as materials based on collagen or gelatine. Still further, the compositions may be introduced into gel-like materials intended to be protecting covers for e.g. anastomoses formed in bowel or vascular surgery.

The invention also relates to a medical device comprising an impregnation or coating comprising a silver compound in the form of a complex of silver and a ligand selected from the group consisting of 5,5-disubstituted hydantoins in which the substituents do not comprise conjugated unsaturated bonds and barbituric acid and derivatives thereof.

Such complex may advantageously be associated with a coating of one or more hydrophilic polymers.

Hydrophilic polymers to be used in the compositions according to the invention are suitably selected from synthetic hydrophilic polymers and derivatives of animal or vegetable hydrophilic polymers. In a preferred embodiment of the invention the hydrophilic polymer is selected from the polysaccharides. Polysaccharides to be used according to the invention are preferably cellulose derivatives. Preferred cellulose derivatives are sodium carboxymethylcellulose and hydroxyethylcellulose.

In another embodiment of the invention the hydrophilic polymer is selected from the alginates. An alginate is preferably the sodium and/or calcium alginate. It has been found to be especially suitable when the alginate has been formed from an alginate comprising an alkali metal such as lithium, sodium, or potassium ions, preferably sodium ions; or ammonium ions that the alginate is subjected to ion exchange using calcium nitrate as this will not give rise to presence of chloride ions which would cause a precipitation of silver in the form of sparingly soluble silver chloride.

In yet another embodiment of the invention the hydrophilic polymer is selected from collagens or fragments thereof. Preferably porcine collagen is used.

In yet further embodiments of the invention the hydrophilic polymer is selected from glucosaminoglycans and proteoglycans.

In still another, preferred embodiment the composition according to the invention is a hydrophilic polymer which forms a gel or xerogel.

The polymers to be used in the compositions of the present invention may be in the form of a polymer forming a network of crosslinked or non crosslinked hydrophilic polymer.

Preferred hydrophilic polymers are optionally modified polysaccharides and preferably from the group of cellulosic derivatives having various substituents. These polymers are readily available from the nature or from synthetic modification. Other preferred polymers are polylactic acid, hydroxypolyesters, polyvinyl ether, polyvinyl alcohol, polyvinylpyorrolidone, polyacrylates, hydrophilic polyurethanes, polymaleic acid, copolymers of anhydrides and polymers of natural origin like glucosaminoglycans, collagen, gelatine and fibrin or the like as well as copolymers or derivatives thereof.

Further, such polymers may be crosslinked into a three-dimensional network.

The concentration of silver in a composition with a hydrophilic polymer according to the invention is preferably from 0.05 to 20% by weight of the dry matter, more preferred from 0.5 to 5% by weight of the dry matter.

Furthermore, the invention relates to a method of producing compositions having antibacterial, antiviral and/or antifungal activity and comprising a complex of silver and a ligand selected from the group consisting of 5,5-disubstituted hydantoins in which the substituents do not comprise conjugated unsaturated bonds and barbituric acid and derivatives thereof in which a silver salt is dissolved in water, a 5,5-disubstituted hydantoin in which the substituents do not comprise conjugated unsaturated bonds or barbituric acid or a derivative thereof is dissolved in water and added to the solution of the silver salt at a controlled pH and the resulting solution is left for a period of from 2 to 100 hours, optionally after adjusting the pH using a value of 7-11, the resulting mixture is isolated and optionally dried and micronised. The isolation may be carried out in analogy to the standard isolation of similar compounds.

The composition according to the invention may be utilised without intermediary drying and optional micronisation and e.g. added directly to a hydrophilic polymer.

Still further, the invention relates to a method of treating or preventing infection in a human being by applying a medical device such as a wound dressing or an ostomy appliance, an incontinence device, or other device such as a catheter comprising a hydrophilic coating; which medical device comprises a stabilised composition having antibacterial, antiviral and/or antifungal activity, said medical device coated with, impregnated with or blended with a complex of silver and a ligand selected from the group consisting of 5,5-disubstituted hydantoins in which the substituents do not comprise conjugated unsaturated bonds and barbituric acid and derivatives thereof.

Yet further, the invention relates to a medical device such as a wound dressing or an ostomy appliance, an incontinence device, or other device such as a catheter comprising a hydrophilic coating; which medical device comprises a stabilised composition having antibacterial, antiviral and/or antifungal activity, said medical device being coated with, impregnated with or blended with a complex of silver and a ligand selected from the group consisting of 5,5-disubstituted hydantoins in which the substituents do not comprise conjugated unsaturated bonds and barbituric acid and derivatives thereof.

An incontinence device of the invention may be a urisheath or a catheter or guide wire comprising a hydrophilic coating or adhesive comprising a composition according to the invention.

An ostomy appliance of the invention may be an ostomy bag or a body side member or any ostomy device such as a closure comprising a composition according to the invention.

The invention is explained more in detail in the working examples below disclosing embodiments and properties of compositions of the invention. It is evident that many variations may be made without diverging from the invention the scope of which is set forth in the appended claims.

Materials and Methods

97% 5,5-Dimethyl-hydantoin (Commercially available from Aldrich)

98% 5,5-Dimethyl barbituric acid (Commercially available from Fluka)

Sodium hydroxide (Analytical Grade, commercially available from Merck)

Purified Water (Demineralised water, conductivity 0.04 micros)

Polyvinyl pyrrolidone—PVP K90 (Commercially available from International Speciality Products)

Hypol 2002 (An isocyanate prepolymer, commercially available from Hampshire Chemical, Inc.)

PE 6200, Surfactant (Commercially available from BASF)

Silver Nitrate powder (63.5% pure silver, commercially available from Johnson Matthey)

Synthesis of Ligands for Complexing with Silver:

1-Acetyl-5,5-dimethyl-hydantoin:

25.6 g 5,5-dimethyl-hydantoin, 50 g acetic anhydride and 5 drops of conc. sulphuric acid is refluxed for 1 h, and evaporated to dryness at reduced pressure. 10 ml Ethanol is added, the slurry is first heated, then cooled in an ice bath and filtered. The solid residue was recrystallised in 100 ml ethanol and dried. Yield 12.3 g (36%)

5,5-Diethyl-hydantoin:

135 g ammonium carbonate, 58.5 g potassium cyanide, 525 g purified water and 64.5 g 3-pentanone is heated for 24 h/75° C. in a closed vessel with vigorous stirring. The vessel is cooled in an ice bath, and the reaction mixture is filtered, the crystals rinsed with ice-water and dried. Yield 45 g (38%)

5,5-Dipropyl-hydantoin:

27 g ammonium carbonate, 11.7 g potassium cyanide, 105 g purified water and 17.1 g 4-heptanone is heated for 24 h/75° C. in a closed vessel with vigorous stirring. The vessel is cooled in an ice bath, and the reaction mixture is filtered, the crystals rinsed with ice-water. The crystals are dissolved in ethanol, 3 g of activated carbon is added, the mixture is stirred for 1 h and filtered. The product is recrystallised from ethanol/purified water and dried. Yield 24.2 g (88%).

5-Methyl-5-isobutyl-hydantoin:

27 g ammonium carbonate, 11.7 g potassium cyanide, 105 g purified water and 15.0 g methyl-isobutyl-ketone is heated for 24 h/75° C. in a closed vessel with vigorous stirring. The vessel is cooled in an ice bath, and the reaction mixture is filtered, the crystals rinsed with ice-water and dried. The crystals are dissolved in 100 ml 1M NaOH, end precipitated with slow addition of 20% $HNO_3$. The mix is filtered and rinsed with purified water. The solid is suspended in 100 ml purified water, stirred vigorously for 1 h, filtered and dried. Yield 13.8 g (54%)

UV Light Stability Test:

1.5 g of complex was placed in a 50 mm Pyrex petri dish. This was covered with a 56 mm Pyrex lid with a UV-cut off at approx. 280 nm and placed 100 mm under a UV lamp (UVASPOT) 400/T 450W metal halide high pressure lamp, Dr. K. Hönle GmbH) for 30 minutes.

The colour was measured, with a Minolta CR300 colour measurement apparatus (CIE-Lab colour coordinates) before (1) and after (2) irradiation. Measurements were made approx. 1 mm above the complex. The distance in colour-space was calculated using the formula $$\text{Dist}=\sqrt{\Delta L^2+\Delta a^2+\Delta b^2}$$, where "L", "a", and "b" are the CIE-Lab Colour Coordinates Solubility for 1:1 Complexes:

Procedure for determination of solubility: 250 mg of the substance to be examined is placed in a 15 ml PP centrifuge tube and 10 ml purified water is added. The tube is placed on a vortex mixer for 1 h (1500 $min^{-1}$) and the tube is centrifuged (3000 $min^{-1}$/30 min). The water is decanted off and discarded, and another 10 ml purified water is added. This is repeated 2 times, and after the third centrifugation, the liquid decanted off is filtered (0.22 mm PVDF), preserved with nitric acid and the silver concentration is determined by atomic absorption spectroscopy after appropriate dilution.

Solubility for 1:X Complexes (Where x Exceeds 1):

0.15 g 1:1 complex was suspended in 10 ml 0.1 M solution of the corresponding sodium hydantoinate (Ligand being in a molar excess of the 1:1 complex), and $C_{Ag}$ is determined with Atomic Absorption Spectroscopy (MS) using a Perkin Elmer A-Analyst 100 apparatus after filtration and appropriate dilution at ambient temperature. In case that this yields in a clear solution the solubility is simply reported as >5.000 mg Ag/l.

Experimental Part

EXAMPLE 1

Determination of solubility of complexes of silver with various ligands. The solubility was determined as stated above and the results are stated in the below Table 1.

TABLE 1

The solubility was determined as mg Ag/l water:

| Silver Complex | Complex Ag:ligand | Solubility mg Ag/l |
|---|---|---|
| Ag/hydantoin | 1:1 | 3 |
| Ag/hydantoin/Na | 1:2 | >5.000 |
| Ag/5,5-dimethyl-hydantoin | 1:1 | 104 |

TABLE 1-continued

| The solubility was determined as mg Ag/l water: | | |
|---|---|---|
| Silver Complex | Complex Ag:ligand | Solubility mg Ag/l |
| Ag/5,5-dimethyl-hydantoin/Na | 1:2 | >5.000 |
| Ag/5,5-diethyl-hydantoin | 1:1 | 260 |
| Ag/5,5-diethyl-hydantoin/Na | 1:2 | >5.000 |
| Ag/5,5-dipropyl-hydantoin | 1:1 | 27 |
| Ag/5,5-dipropyl-hydantoin/Na | 1:2 | >5.000 |
| Ag/1-acetyl-5,5-dimethyl-hydantoin | 1:1 | 1.100 |
| Ag/5-isobutyl-5-methyl-hydantoin | 1:1 | 12 |
| Ag/5,5-diphenyl-hydantoin | 1:1 | 11 |
| Ag/5,5-diphenyl-hydantoin/Na | 1:2 | 0.7 |

EXAMPLE 2

Preparation of Silver Complexes

Silver hydantoinate: 12 g hydantoin and 100 ml 1 M NaOH was dissolved in 100 ml purified water. 16.3 g $AgNO_3$ dissolved in 50 ml purified water is added slowly with stirring. The suspension is left with stirring for 2 h and filtered. The white solid is resuspended in 200 ml purified water, stirred for 2 h, filtered, washed with acetone and dried. Yield 19.0 g (96%)

Silver 5,5-dimethyl-hydantoinate: 12.3 g 5,5-dimethyl-hydantoin and 4.2 g NaOH is dissolved in 150 ml purified water. 16.3 g $AgNO_3$ dissolved in 50 ml purified water is added slowly with stirring. The suspension is left with stirring for 2 h and filtered. The white solid is resuspended in 200 ml purified water, stirred for 2 h, filtered, washed with acetone and dried Silver 5,5-diethyl-hydantoinate: 1.87 g 5,5-diethyl-hydantoin and 10.0 ml 1 M NaOH is dissolved in 20 ml purified water. 1.70 g $AgNO_3$ dissolved in 10 ml purified water is added slowly with stirring. The suspension is left with stirring overnight, filtered, washed with purified water and acetone and dried. Yield 2.54 g (97%)

Silver 5,5-dipropyl-hydantoinate: 2.21 g 5,5-dipropyl-hydantoin and 10.0 ml 1 M NaOH was dissolved in 40 ml purified water. 1.70 g $AgNO_3$ dissolved in 10 ml purified water is added slowly with stirring. The suspension is left with stirring overnight, filtered, washed with purified water and acetone, resuspended in 50 ml acetone, filtered and dried. Yield 2.18 g (75%)

Silver 5-methyl-5-isobutyl-hydantoinate: 1.70 g 5-methyl-5-isobutyl-hydantoin was dissolved in a surplus of 25% $NH_3$ (aq) and 1.70 g $AgNO_3$ in 20 ml purified water is added slowly with stirring. The suspension is stirred overnight, and the purified water is removed at reduced pressure. The solid is suspended in purified water, filtered, washed with purified water and acetone and dried. Yield 2.69 g (97%)

Silver 1-acetyl-5,5-dimethyl-hydantoinate: 8.51 g 1-acetyl-5,5-dimethyl-hydantoin was dissolved in 55 ml 1M NaOH and 100 ml purified water. 8.49 g $AgNO_3$ in 40 ml purified water is added slowly with stirring. The suspension is stirred for another 20 min, cooled with ice, filtered, washed with cold purified water and dried.

Silver allantoinate: 1.90 g (12 mmol) allantoin was dispersed in 20 ml distilled purified water and 10.0 ml 1 M NaOH is added while stirring at ambient temperature. Allanthoin was in a slight excess to prevent strong alkalinity. 1.70 g silver nitrate (10 mmol) in purified water is added under vigorous stirring while white precipitate of the silver complex is form. This is filtered, dried and milled.

EXAMPLE 3

Determination of Relative UV Light Stability of Complexes

Silver allantoinate: attempts to make the complex according to U.S. Pat. No. 2,336,131 gave a product that discoloured extremely easily (rendering a UV light-stability test meaningless), so a modified procedure was adopted:

1.897 g allantoin (12 mmol) was suspended in 20 ml purified water, and 10.0 ml 1M NaOH (10 mmol) Was added. 1.70 g $AgNO_3$ (10 mmol) in 10 ml purified water was added slowly with stirring, and the suspension filtered, rinsed with purified water and acetone and dried yielding a hard solid that was white without traces of discoloration. This was crushed in a mortar and used as was.

The results of the tests for UV stability is stated in the below Tables 2 and 3:

TABLE 2

| Visual evaluation of complexes after UV-irradiation: | |
|---|---|
| Ag-5,5-diphenyl-hydantoin 1:1 | Dark brown discolouration |
| Ag-5,5-dimethyl-hydantoin 1:1 | White/no trace of discolouration |
| Ag-5,5-diethyl-hydantoin 1:1 | White/no trace of discolouration |
| Ag-5-methyl-5-isobutyl-hydantoin 1:1 | White/no trace of discolouration |
| Ag-allantoin 1:1 | Dark brown/heavily discoloured |
| Ag-hydantoin 1:1 | Dark brown/heavily discoloured |

TABLE 3

| Colour measured with a Minolta CR300 colour measurement apparatus | | | | | | | |
|---|---|---|---|---|---|---|---|
| Compound | L1 | a1 | b1 | L2 | a2 | b2 | Dist. |
| Ag-5,5-dimethyl-hydantoin 1:1 | 94.96 | 0.29– | 0.12 | 96.84 | 0.31– | 0.39 | 1.90 |
| Ag-5,5-diethyl-hydantoin 1:1 | 96.76 | 0.04– | 0.67 | 94.05 | 0.35– | 2.03 | 3.05 |
| Ag-5-methyl-5-isobutyl-hydantoin 1:1 | 92.4 | 0.03 | 0.42 | 92.65 | 0.16– | 1.74 | 1.36 |
| Ag-hydantoin 1:1 | 96.67 | 0.06 | 2.62 | 26.03 | 10.75 | 12.84 | 72.17 |
| Ag-5,5-diphenyl-hydantoin 1:1 | 93.05 | 0.71– | 2.59 | 38.71 | 21.06 | 33.81 | 66.34 |
| Ag-allantoin 1:1 | 92.98 | 0.53– | 2.3 | 32.7 | 14.71 | 28.41 | 67.44 |

Compounds according to the production in example 4 were assessed for stability against UV-light (wave length >280 nm). Milled powders were spread in a 1 mm thick layer in ordinary petri dishes and illuminated by the UV-light for 30 minutes.

The results show that the compounds of the invention show a clearly better stability against discolourisation than known compounds, i.e. having a distance in CIE-lab colour space of <25.

EXAMPLE 4

Preparation of Stabilised Silver Solution (SSS)

In one litre of purified water 79.2 grams (0.6 moles) of 5,5-dimethyl hydantoin, 17.2 grams (0.43 moles) of sodium hydroxide and 34 grams (0.2 moles) of silver nitrate was dissolved (the silver nitrate and the 5,5 Di Methyl Hydantoine were dissolved separately and mixed when the two solutions were clear to avoid precipitation). This solution was designated Stabilised Silver Solution (SSS). The Silver concentration in the SSS was app. 2% w/w.

The SSS is simple to incorporate in both wet and dry wound care products, due to the stability of the SSS for obtaining antibacterial wound care dressings.

In the below four examples is demonstrated how the SSS can be incorporated into foams, amorphous hydrogels and hydrogel sheets. It is simple to use other formulations for preparing products in all the 3 product categories mentioned above. The SSS can be included in almost any other product category like films, alginates, hydrofibres, gauze etc.

EXAMPLE 5

Incorporation of SSS in a Foam

This example demonstrates how the SSS may be incorporated into a Foam product, which is suitable for treating colonised wounds.

EXAMPLE 5A

Incorporation of SSS in a foam during the foaming process.

The SSS produced above was mixed with purified water and PE 6200 to form a homogeneous water phase for the foaming reaction. The water was mixed with Hypol 2002 and while the mixture still is a fluid, the fluid is transformed into a sheet, and the mixture was allowed to rise into a foam dressing. When the foaming reaction had ended (after app. 15 minutes), the foam sheet was dried in an oven at 110° C. for 10 minutes.

In table 4 below, the composition by weight in grams of the different constituents is stated.

TABLE 4

Composition of foam products according to the invention wherein SSS is incorporated during foaming.

| Ingredient | Example 6A1 | Example 6A2 |
|---|---|---|
| SSS | 5 | 20 |
| Purified water | 15 | 0 |
| PE 6200 | 0.2 | 0.2 |
| Hypol 2002 | 20 | 20 |

The resulting antibacterial foams were sterilised at 30 kGy.

EXAMPLE 5B

Incorporation of SSS in foam after the foaming process.

A foam sheet was prepared in a similar as described above, but without adding SSS in the process. The amounts of the different ingredient in grams is stated in the below table 5.

TABLE 5

Composition of a foam produced without adding silver in the foaming process

| Ingredients | Amount (grams) |
|---|---|
| Purified water | 20 |
| PE 6200 | 0.2 |
| Hypol 2002 | 20 |

Foam prepared above was immersed in solutions of different concentrations of the SSS (prepared by mixing SSS with different amounts of purified water) and allowed to absorb fluid until it was completely saturated. Then, the fluid was squeezed out of the foam leaving 200% absorbed fluid as compared to the dry weight of the foam. Finally the foam was dried in an oven at 110° C. to a moisture content below 10% w/w (15 minutes). The composition of the SSS/water mixtures appear from the below Table 6.

TABLE 6

SSS/Water mixtures for the incorporation of silver in foam according to the invention.

| Ingredients | Example 6B1 | Example 6B2 |
|---|---|---|
| SSS (grams) | 10 | 40 |
| Purified water (grams) | 70 | 40 |

The final antibacterial foams were sterilised at 30 kGy.

The silver content of each foam sample as determined by Atomic Absorption appear from the below table 7:

TABLE 7

| Sample no. | Silver content (mg/g) |
|---|---|
| 6A1 | 49 |
| 6A2 | 18 |
| 6B1 | 61 |
| 6B2 | 23 |

EXAMPLE 6

Incorporation of SSS an Amorphous Hydrogel

This example demonstrates how the stabilised silver solution can be incorporated in an amorphous hydrogel for treatment of Wounds. It is also possible to use other hydrogel formulations in order to obtain an antibacterial amorphous hydrogel.

Preparation of an Amorphous Hydrogel According to the Invention.

A hydrogel was prepared by mixing SSS prepared above, PVP and purified water in a beaker. The composition of the hydrogel prepared is presented in the below Table 8:

TABLE 8

Composition of the hydrogels according to the invention:

| Ingredients | Sample 7 |
|---|---|
| Purified water | 180 grams |
| PVP | 12 grams |
| SSS | 20 grams |

After complete solubilisation of the PVP, the solution was transferred into a syringe and sent to electron beam irradiation (2×20 kGy). After sterilisation the gel was squeezed out of the syringe and was in the form of gel particles (an amorphous gel).

EXAMPLE 7

Preparation of Hydrogel Sheets Comprising Diethyl Hydantoin and Dimethyl Barbiturate

EXAMPLE 7A

Preparation of a Stabilised Silver Solution Comprising Diethyl Hydantoin.

A stabilised silver solution was prepared as described in example 4, but using 5,5-diethyl hydantoin instead of dimethyl hydantoin in the same molar amount. The silver concentration was 0.25% instead of 2% w/w (adjusted with extra purified water giving the same mole ratio between silver, diethyl hydantoin and sodium hydroxide as in example 5).

EXAMPLE 7B

Preparation of a Stabilised Silver Solution Comprising Dimethyl Barbiturate

A stabilised silver solution was prepared as described in example 4, but using 5,5-dimethyl barbiturate instead of dimethyl hydantoin in the same molar amount.

The silver concentration was 0.25% instead of 2% w/w. The amount of sodium hydroxide was adjusted to a level ensuring that the molar ratio between sodium hydroxide and silver nitrate was 3.

Hydrogel sheets according to the invention were prepared by mixing the stabilised solution of 5,5-diethyl hydantoin or 5,5-dimethyl barmiturate obtained above, PVP and purified water in a beaker After complete solubilisation of the PVP in the stabilised silver solution and purified water, the solution was transferred into a sheet shape (5 mm thick) and sent to electron beam irradiation (2×20 kGy).

The compositions of the hydrogel sheets are stated in the below Table 9

TABLE 9

| Ingredients | Sample 8A | Sample 8B |
|---|---|---|
| Solution of diethyl hydantoin | 160 grams | 0 grams |
| Solution of dimethyl barbiturate | 0 grams | 160 grams |
| PVP | 12 grams | 12 grams |
| Purified water | 40 grams | 40 grams |

The silver content in the Hydrogel sheets were app. 0.2%

EXAMPLE 8

Incorporation of SSS in an Alginate Fabric

A stabilised silver solution was prepared as in example 5, but using 63.8 grams of Water, 21.90 grams of 5,5-Di Methyl Hydantoin, 4.80 grams of Sodium Hydroxide and 9.50 grams of Silver Nitrate.

To this solution was added 50 grams of PEG 600 and 450 grams of 96% ethanol, giving a final silver concentration of 1 w/w %.

Pieces of 100 square cm of an alginate non woven fabric (Algisite M from S+N) were soaked in the above solution until saturation (about 20 grams solution per piece) and were squeezed in such a manner that the pieces retained 5 grams of the solution corresponding to 50 mg Silver.

EXAMPLE 9

Antimicrobial Effect

Demonstration of Antimicrobial Effect of Compounds According to the Invention

Isosensitest agar plates were inoculated with *Ps. aeruginosa* or *St. aureus* and incubated for 24 hr at 37° C. 10 mm Circles of a sample of a composition according to the invention were placed on to the agar plates (when testing the amorphous hydrogel, a circular hole of a diameter of 10 mm was cut out of the agar plate and filled with the hydrogel). After 24 hours, the zone of inhibition was measured and the samples were moved to fresh inoculated and incubated agar plates. The zone of inhibition was measured after additional 24 hours (corresponding to a service time of 48 hours). This was repeated for additional 24 hours (corresponding to a service time of 72 hours).

The results are summarised in the below Table 10 Table 10

TABLE 10

| Microbial effect (diameter of zone of inhibition in mm) | | | | | | |
|---|---|---|---|---|---|---|
| | *Ps. Aeruginosa* | | | *St. Aureus* | | |
| Sample no | 24 hours | 48 hours | 72 hours | 24 hours | 48 hours | 72 hours |
| 5A1 | 10.0 | 14.3 | 16.3 | 10.0 | 10.0 | 10.0 |
| 5A2 | 14.0 | 20.0 | 17.7 | 13.0 | 14.0 | 10.3 |
| 5B1 | 11.0 | 10.0 | 10.0 | 10.0 | 0.0 | 0.0 |
| 5B2 | 16.0 | 19.0 | 16.7 | 16.0 | 16.3 | 14.0 |
| 6 | 21.0 | 45.7 | 23.3 | 21.3 | 15.0 | 14.3 |
| 7A | 16.0 | 20.0 | 24.0 | 14.5 | 14.5 | 14.5 |
| 7B | 14.0 | 19.5 | 23.0 | 16.0 | 14.0 | 14.0 |
| 8 | 16.0 | 12.0 | 10.0 | 18.0 | 13.0 | 12.0 |

The results show that wound care products comprising silver complexes of the invention show an antibacterial activity for more than 72 hours.

From Examples 5A and 5B it appears that the total load of silver influences the antimicrobial properties.

The invention claimed is:

1. A stabilized composition having antibacterial, antiviral and/or antifungal activity, said composition containing silver ions in complex with a ligand, wherein said composition comprising a complex of silver ions; and a ligand selected from the group consisting of:

5,5-dimethyl-barbituric acid or 1,5,5-trimethyl-barbituric acid, wherein said silver ions are stabilized against reduction to free silver in a hydrophilic environment and the composition has a solubility in water greater than 10 mg Ag/l.

2. A composition as claimed in claim 1, wherein said composition contains a second silver compound with a solubility less than 10 mg Ag/l.

3. A composition as claimed in claim 1, wherein said composition is mixed into a polymer composition.

4. A composition according to claim 3, wherein the polymer is a hydrophilic polymer.

5. A composition as claimed in claim 4, wherein the hydrophilic polymer forms a gel, a foam or a xerogel.

6. A composition as claimed in claim 4, wherein said composition is mixed into an alginate.

7. A composition as claimed in claim 1, wherein the concentration of silver is from 0.1 to 20% by weight of the dry matter.

8. A method of producing the composition of claim 1, said method comprising the steps of:

1) dissolving a silver salt in water;

2) adding a ligand selected from the group consisting of 5,5-dimethyl-barbituric acid or 1,5,5-trimethyl-barbituric acid to the solution of the silver salt at a controlled pH;

3) leaving the resulting solution for a period of between about 2 to 100 hours;

4) optionally adjusting the pH to a value of 7-11;

5) isolating the resulting mixture; and 6) optionally drying and micronizing the mixture.

9. A medical device which comprises the the composition of claim 1.

10. A method of treating infection in a human being by applying the medical device of claim 9.

11. The medical device of claim 9, wherein said device is a catheter having a hydrophilic coating.

12. The method of treating infection in a human being of claim 10, wherein said medical device is a catheter having a hydrophilic coating.

13. The medical device according to claim 9, wherein the medical devices is selected from the group consisting of a wound dressing, an ostomy appliance, and an incontinence device.

* * * * *